United States Patent [19]

Xavier

[11] Patent Number: 5,458,631
[45] Date of Patent: * Oct. 17, 1995

[54] IMPLANTABLE CATHETER WITH ELECTRICAL PULSE NERVE STIMULATORS AND DRUG DELIVERY SYSTEM

[76] Inventor: Ravi Xavier, 748 Lakeside Dr., North Palm Beach, Fla. 33408

[*] Notice: The portion of the term of this patent subsequent to Jun. 9, 2009 has been disclaimed.

[21] Appl. No.: 216,501

[22] Filed: Mar. 22, 1994

Related U.S. Application Data

[63] Continuation of Ser. No. 919,460, Jul. 27, 1992, abandoned, which is a continuation-in-part of Ser. No. 378,324, Jul. 11, 1989, abandoned, which is a continuation-in-part of Ser. No. 294,380, Jan. 6, 1989, abandoned.

[51] Int. Cl.⁶ ............................. A61N 1/04; A61M 25/00
[52] U.S. Cl. ........................... 607/117; 128/642; 604/21; 604/49; 604/51; 604/891.1
[58] Field of Search ................................ 607/116, 117, 607/118, 122; 128/642, 898, 899; 604/890.1, 891.1, 20, 21, 48–51, 280–283

[56] References Cited

U.S. PATENT DOCUMENTS

| | | | |
|---|---|---|---|
| 3,923,060 | 12/1975 | Ellinwood, Jr. ..................... | 604/891.1 |
| 4,073,287 | 2/1978 | Bradley et al. ..................... | 128/642 |
| 4,379,462 | 4/1983 | Borkan et al. ..................... | 607/117 |
| 4,544,371 | 10/1985 | Dormandy, Jr. et al. ............. | 604/891.1 |
| 4,549,556 | 10/1985 | Tarjan et al. ..................... | 607/117 |
| 5,026,344 | 6/1991 | Dijkstra et al. ..................... | 604/891.1 |
| 5,031,618 | 7/1991 | Mullett ........................... | 607/59 |
| 5,041,107 | 8/1991 | Heil, Jr. ........................... | 604/891.1 |
| 5,085,644 | 2/1992 | Watson et al. ..................... | 604/891.1 |
| 5,119,832 | 6/1992 | Xavier ............................ | 607/117 |
| 5,121,754 | 6/1992 | Mullett ........................... | 607/117 |
| 5,255,691 | 10/1993 | Otten ............................. | 607/117 |

FOREIGN PATENT DOCUMENTS

| | | |
|---|---|---|
| 3602219 | 7/1987 | Germany . |
| 1005796 | 3/1983 | U.S.S.R. . |

*Primary Examiner*—Krista M. Zele
*Attorney, Agent, or Firm*—Kenneth W. Iles

[57] ABSTRACT

A catheter intended to be implanted in the epidural space of a patient for relief of pain, either temporarily or permanently, includes four circumferential ring electrodes connected to terminals by fine wires embedded in the side wall of the catheter for attachment to a conventional electric pulse generator and a hollow elongated body having a lumen therethrough with an injection portal at the proximal end and an aperture at the distal end for continuously administering a pain-relieving agent in a liquid form. The agent may be a narcotic or anesthesia. In the permanently implantable embodiment, the catheter includes an implantable pulse generator and an implantable drug reservoir, both of which can be repeatedly programmed while implanted. Methods for treating pain using the catheter include electrical stimulation, the use of narcotics, or anesthesia, which can be administered in any order, or simultaneously as empirically determined to provide the best pain relief for each patient.

19 Claims, 2 Drawing Sheets

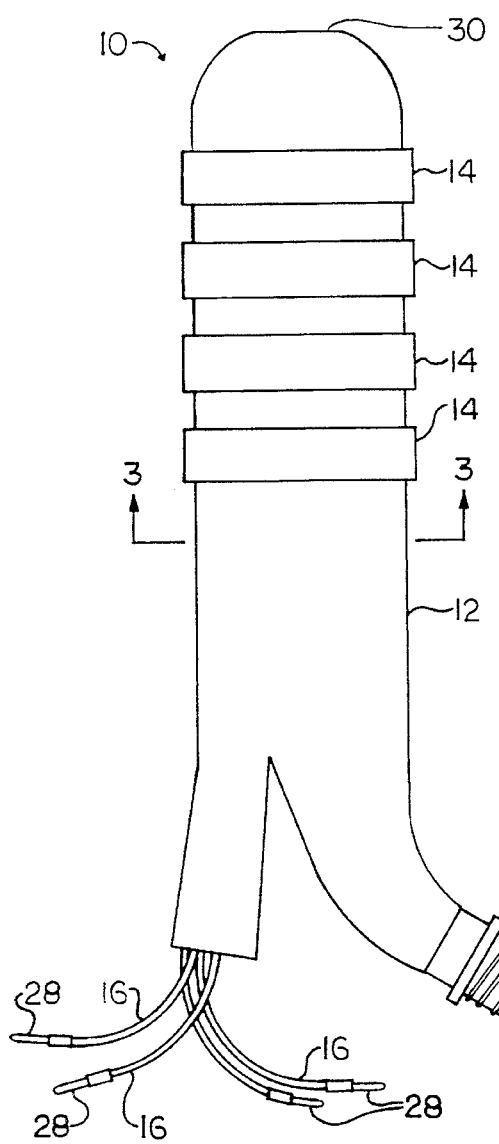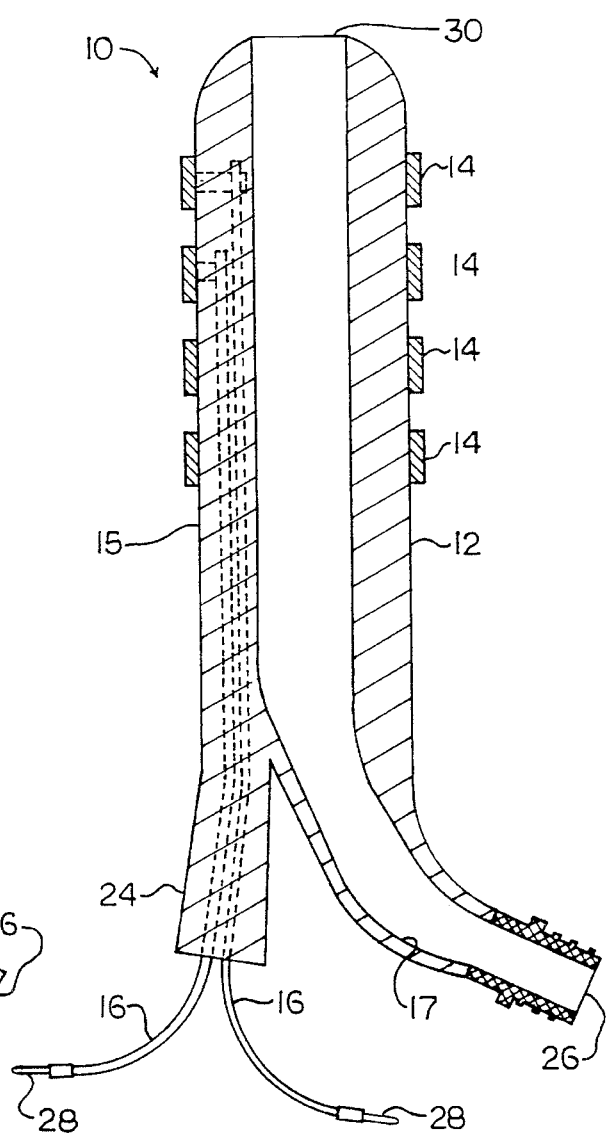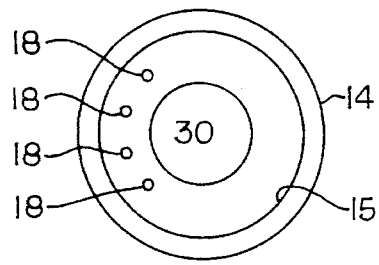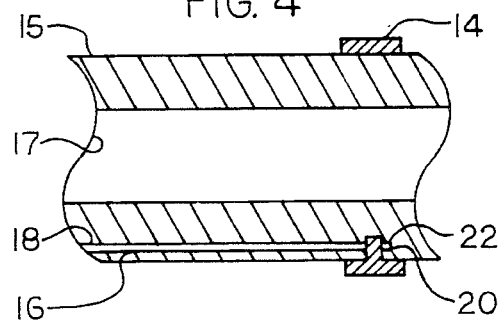

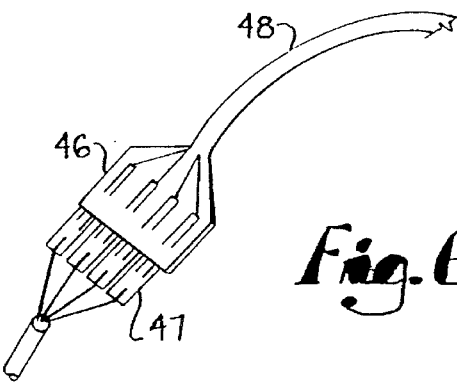
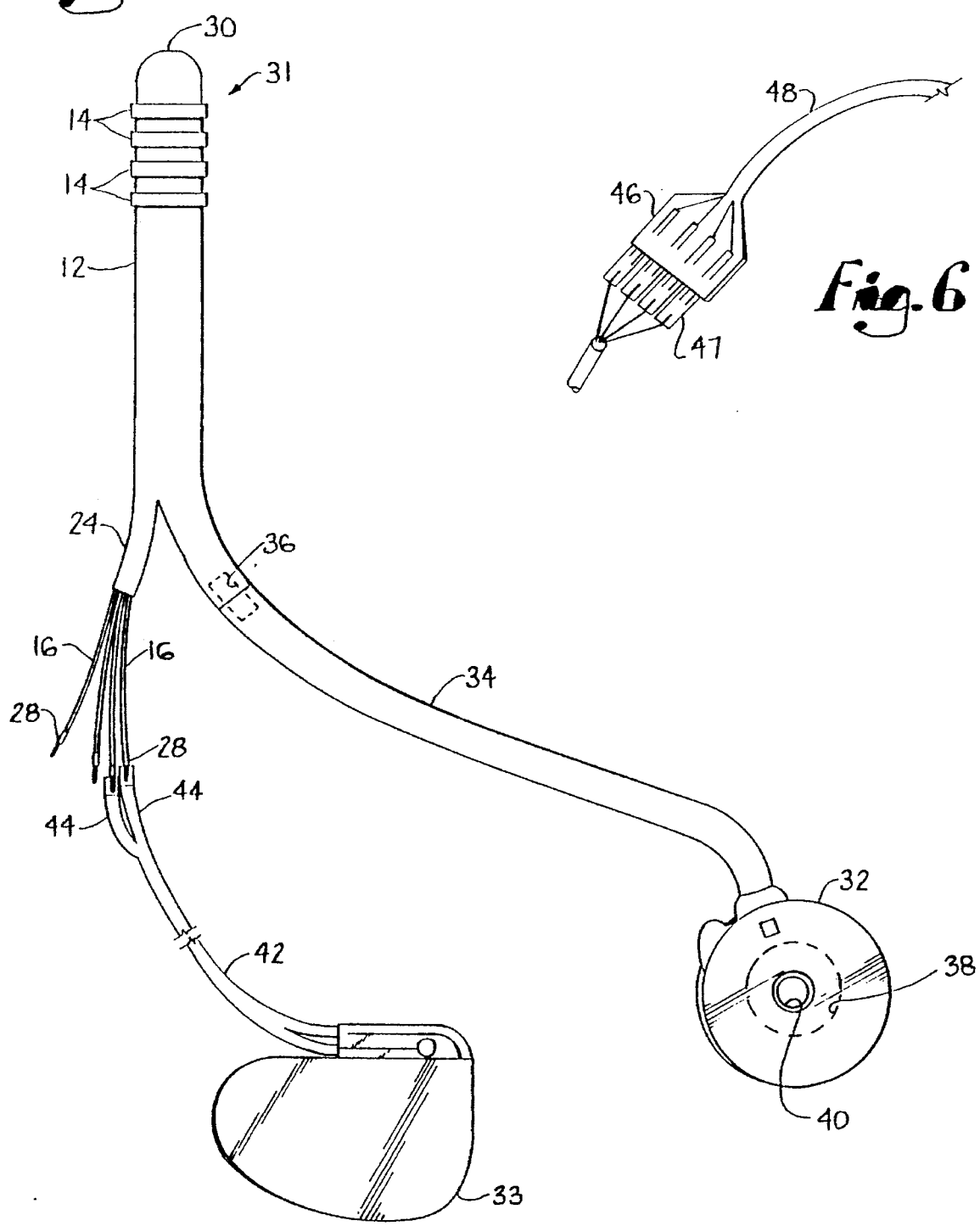

IMPLANTABLE CATHETER WITH ELECTRICAL PULSE NERVE STIMULATORS AND DRUG DELIVERY SYSTEM

CROSS REFERENCE TO RELATED APPLICATIONS

This application is a Continuation of Ser. No. 07/919,460, filed Jul. 27, 1992, now abandoned, which is a continuation-in-part of Ser. No. 07/378,324, filed Jul. 11, 1989, now abandoned, which is a continuation-in-part of Ser. No. 07/294,380, filed Jan. 6, 1989, now abandoned.

BACKGROUND OF THE INVENTION

1. Field of the Invention

The present invention is directed to a catheter having a lumen for delivering drugs into the epidural space of a patient and electrodes for the relief of pain. More particularly, the present invention is directed to such a catheter that can be implanted in the patient temporarily or permanently. The permanent implantation embodiment includes a self-contained electrical pulse generator and a drug pump with a reservoir.

2. Description of Related Art

Electrical stimulation of the spinal column through electrodes implanted in the epidural space has been found useful in controlling pain. The use of injected anesthetics or narcotics has been found useful in the temporary relief of pain. In some instances, the local anesthetic or the narcotic is administered into the epidural spaces along the spinal column. These and other techniques are used to control intra-operative pain, post-operative pain and chronic pain states, such as those that might result from certain cancers. Such techniques as currently practiced, however, leave many patients without satisfactory pain relief.

This failure is result of the characteristics of the modalities for pain control and of the nerves that carry pain impulses. The nerve fibers carrying pain impulses to the spinal cord are classified into three major groups according to their speeds of conduction. Type A nerve fibers carry pain impulses at the rate of about 30 to 120 meters per second. Type B nerve fibers carry pain impulses at the rate of about 5–15 meters per second. Type C nerves carry pain impulses most slowly of all, about 0.1 to 2 meters per second. These fibers all relay impulses through an area in the spinal cord called the substantia gelatinosa. From this site, the nerve fibers are projected to the brain. The three primary modalities for pain control and their primary disadvantages are as follows.

First, local anesthetics may be injected into the epidural space. Local anesthetics act by blocking the transmission of pain impulses in types A, B, and C nerve fibers. Local anesthetics typically, however, relieve pain only a relatively short time and if large amounts are injected into the epidural space to achieve longer term pain relief, the local anesthetic is absorbed into the blood stream and leads to anesthetic toxicity. Consequently, typical anesthetics must be administered every hour or two. This requirement is labor intensive, provides numerous opportunities for serious treatment errors, leaves the patient in pain much of the time as the effectiveness of a dose fades, and may require repeated penetration of the epidural space, which causes scarring. Second, narcotics, such as morphine sulfate, or methadone, may be injected into the epidural space. Narcotics act by modulating the impulse transmission at the substantia gelatinosa. Narcotics are, however, extremely dangerous and may well spread upwards into the brain and lead to the arrest of breathing, and to death. Narcotics typically bring pain relief within from about 12–25 minutes and provide continuous pain relief for about 6–18 hours, depending on the particular narcotic used and the type of pain being treated. Because narcotics may be extremely addictive, physicians generally prefer to use non-narcotic pain relievers whenever possible. In addition, patients treated with epidural narcotics develop a tolerance for these drugs in which no amount of narcotic administered into the epidural space will effectively control pain, leaving the physician no option for relieving the patient's pain. Withholding the narcotics causes the state of tolerance to disappear after some time, and narcotic therapy can then be effectively resumed. In the meantime, however, other treatments must be resorted to if any pain relief is to be provided.

Third, an optimal amount of electrical stimulation of the spinal cord indirectly through the epidural spaces is used to relieve pain, but acts almost exclusively on the pain impulse traffic along the type C nerve fibers in the spinal nerves, leading to only a 50%–60% reduction in perceived pain. This modality is used in the treatment of pain from chronic inflammation, chronic pain from cancer, old injuries, nerve injuries, and so forth and can be permanently implanted, complete with its own subcutaneous power supply, for example, Trojan et al. U.S. Pat. No. 4,5349,556. Although it is useful for many patients, in many other patients electrical epidural nerve stimulation does not provide full, or even satisfactory pain relief.

In addition, in the case of an injected pain-relieving agent, whether local anesthetics or narcotics, the drugs quickly relieve pain but their pain killing ability dissipates over time due to absorption of the pain reliever by the body, which metabolizes the agent. Thus, the pain-relieving agent must be administered periodically and frequently. Typically, either local anesthetics or narcotics are administered every 2–6 hours (although some narcotics may provide pain relief for up to about eighteen hours in some cases). Even more importantly, it results in wide undulations in the level of pain experienced by the patient. When the anesthetic or narcotic is first administered, nearly all the pain vanishes. With the passage of time, however, the pain returns before the next dose is given. If doses are spaced closely enough to prevent the recurrence of pain, overdosing the patient may occur.

During surgical operations, anesthesia must be administered through a different method than is used to control post-operative pain. In some cases, even in a hospital, overdoses of narcotics lead of the deaths of patients.

Thus, it is clear that the prior art of pain relief includes some significant disadvantages.

Therefore, a need exist for a device and a process or method that achieves effective full-time satisfactory relief from serious pain; that reduces the likelihood of an overdose of an anesthetic or narcotic; and that permits application of a uniform dosage across time; and that permits the physician to establish anesthesia for surgery as well as to control post-operative pain using the same device for both functions; and that allows the physician to treat a patient with narcotics until tolerance develops and to easily replace the narcotic treatment with other effective treatments until the tolerance disappears, and then to easily resume narcotic treatment, all requiring a single penetration of the epidural space; and to provide such a pain-relieving device that can be implanted either temporarily or permanently.

SUMMARY OF THE INVENTION

Accordingly, it is primary object of the present invention to provide a device and a process for achieving effective and satisfactory relief from severe pain temporarily or permanently.

It is a further object of the present invention to provide such a device that reduces the likelihood of an overdose of an anesthetic or narcotic.

It is a further object of the present invention to provide a device that can be used to establish anesthesia during a surgical operation as well as to reduce post-operative pain.

It is a further object of the present invention to provide such a device that can be implanted in the patient, either temporarily or permanently.

It is a further object of the present invention to provide a device that permits the physician to easily overcome the effects of tolerance developed during narcotic therapy. It is a further object of the present invention to provide a device for achieving these ends that requires only a single penetration of the patient's epidural space, thereby reducing scarring.

These and other objects of the present invention are achieved by providing a catheter comprising an elongated body having a hollow bore, or lumen, therethrough, with the lumen having a distal end and a proximal end with a first opening in the distal end and a second opening in the proximal end, at least two ring electrodes, but preferably four, equally spaced from the distal end of the body, and a separate wire connecting each of the electrodes to a separate terminal. In a preferred embodiment, the wires are separately embedded in the side wall of the elongated hollow body, which is preferably basically cylindrical in shape. The electrodes are silver, iridium, or platinum. Platinum is preferred because less body tissue grows around and on it, providing better electrical conduction and better pain relief through electrical pulse stimulation over a long period of time. The wires connecting the ring electrodes to an electrical pulse generator are preferably stainless steel. The proximal end of the lumen includes an injection portal, which is adapted to receive a conventional syringe in sealing frictional engagement (for example, a Luer-Lok (Registered Trademark) threaded fitting), in the preferred embodiment intended for temporary use (several days). The injection portal deviates away from the longitudinal axis of the elongated hollow body, or catheter, as does an electrode casing for holding the wires and keeping them free from the catheter itself. In this embodiment, the injection portal, the wires, and the electrode casing connected to the wires penetrate the skin and remain external to the patient during use, while the distal end, or working end, of the catheter is embedded in the epidural space.

In this temporarily implantable embodiment, the device is inserted through the skin a distance of about 10–15 centimeters (cm) to lie in the epidural space, with the rest of the apparatus left protruding from the patient. The catheter is preferably about 90 cm long and about 17–19 gauge outside diameter. The device is inserted in the patient through a larger needle by well known conventional techniques. In an alternative embodiment, intended for permanent use, the catheter includes a small battery-operated electrical pulse generator having a lead set attached to the wires that run through the side wall of the catheter to the ring electrodes. This second, or permanently implantable catheter, further comprises a self-contained drug pump having an integral drug reservoir connected to the lumen by a small catheter. The reservoir further includes a small membrane through which drugs may be injected into the reservoir while it is under the patient's skin. In a preferred embodiment, the drug pump includes its own battery power supply and will continuously deliver a desired dose of drugs through the catheter into the epidural spaces. The pump is fully programmable while embedded in the patient, as will be described below in detail, and its reservoir holds about a 20–30 day supply of the treatment drug. The permanently implantable device is fully self-contained and may be left in the patient permanently. The precise treatment modality desired may be changed while the apparatus is inside the patient.

In either embodiment, the elongated hollow body may be made from any convenient durable flexible and physiologically inert material such as polyurethane or medical grade silicon, and preferably is made from a substantially inert low-friction substance such as polytetrafluoroethylene (hereinafter "PTFE")(Teflon non-stick material (Registered Trademark)).

In use, electricity is pulsed through two of the four preferred terminals, and hence through two of the ring electrodes that are connected to form a complete electrical circuit, and the patient's epidural space, where it relieves pain in the type C nerves. The two electrodes that provide the best pain relief are chosen through well known means. The remaining two electrodes may not be connected to any terminals. More than four electrodes may be used if desired. Concurrently, a pain-relieving agent, such as an anesthetic or narcotic, may be delivered through the lumen by injection or other means, such as an I.V. type slow delivery. In another method of application, an intravenous-type solution feed bottle is attached to the injection portal, allowing a steady slow flow of a dilute solution of a liquid pain-relieving agent through the lumen and into the epidural space, where the agent acts to relieve pain transmitted by all three types of nerves while avoiding the danger of overdose. Use of this catheter leads to pain reductions of about 95%.

Several methods for relieving pain may be employed utilizing the catheter. The lumen may be used to deliver anesthesia, anesthetic, narcotic substances, or other pain-reliving agents. For example, a local topical anesthetic may be conventionally applied to a patient, and the catheter them implanted into the patient's epidural space. Then an anesthetic may be introduced through the lumen to permit painless surgery. Following surgery, the ring electrodes may be employed to use electrical stimulation through the electrodes to relieve pain, and they may also be used in conjunction with any anesthesia, anesthetic, or narcotic, either simultaneously or at different times. These four basic treatment modalities of anesthesia, anesthetics, narcotics, and electrical stimulation may be used in any order or in conjunction with one another to provide the best pain relief, subject to accepted medical practice.

It is intended that the temporary use catheter be implanted for, at most, several days, primarily for treatment of pain during and after surgery. The permanently implantable embodiment of the catheter may be implanted in the patient for life for control of chronic intractable pain.

Other objects and advantages of this invention will become apparent form the following description taken in connection with the accompanying drawings, wherein is set forth by way of illustration and example, a preferred embodiment of this invention.

BRIEF DESCRIPTION OF THE DRAWINGS

FIG. 1 is a side elevation of a temporary catheter according to the present invention.

FIG. 2 is a sectional side elevation of the catheter of FIG. 1.

FIG. 3 is a cross section taken along lines 3–3 of FIG. 1, taken along a line such that only two of the four wires and electrodes are visible.

FIG. 4 is a fragmentary cross section of the a catheter of FIG. 1, illustrating the connection of a wire with an electrode.

FIG. 5 is a front elevation of a permanent catheter according to the present invention, illustrating the self-contained electrical pulse generator, the drug pump, and the catheter.

FIG. 6 is a front elevation of a preferred electrical connector block for electrically connecting the ring electrodes of the catheter to the pulse generator.

DESCRIPTION OF THE PREFERRED EMBODIMENT

Referring to FIG. 1, there is shown an epidural catheter with nerve stimulators, or catheter 10, comprising an elongated hollow tubular body 12, which incorporates two different systems for inducing anesthesia, which are: (1) electrical pulse stimulation; and (2) introduction of a liquid pain-relieving agent into the patients's body.

Four circumferential ring electrodes 14 coat the exterior side wall 15 of the catheter 10. One ring electrode 14 is located approximately 1 cm from the distal end of the catheter 10 and the four ring electrodes are equally spaced from the starting point. In this temporary use embodiment, the electrodes are 3 mm wide and about 5–6 mm apart. The ring electrodes 14 are made from a highly electrically conductive metal that does not react extensively with bodily fluids, preferably silver, gold, or platinum. Platinum is the preferred metal because it reduces epidural fibrosis and maintains good electrical connection to the bodily tissues. Each ring electrode 14 comprises an outer band that is adapted to conduct electricity into the tissues of the epidural space. It is important that the electrodes be smooth to prevent abrasion of the tissues during insertion and removal of the catheter 10.

The electrodes 14 may be made from an electrically-conductive metallic powder, such as silver metal or platinum metal precipitated in an analytical reagent mixed with an inert silicon medical adhesive.

The catheter body 12 is preferably made from a physiologically inert radiopaque material such as medical grade silicon, polyurethane, or polytetrafluoroethylene (PTFE), so that the catheter body 12 will be visible in X-rays. If the catheter body 12 is not made wholly from PTFE, it may be coated with PTFE or another substance having similar properties, to reduce the friction upon insertion into the patient.

When the elongated hollow body 12 of the catheter 10 is made from a physiologically inert medical grade silicon elastometer, the right electrodes 14 can be formed by adding a dispersion agent solvent, such as xylene, toluene, freon, or other silicon solvent to the mixture of the powered metal and silicon medical adhesive to provide a substantially liquid mixture. The resulting mixture may be applied to the surface of the catheter 10 in the desired patterns. After the reagent solvent evaporates and the adhesive cures, the ring electrodes 14 are permanently bonded to the catheter 10. Preferably, relatively little adhesive is used, the ratio of adhesive to silver being between approximately 1:3 to 1:5 by weight. This low ratio of adhesive to silver increases the electrical conductivity of the ring electrodes 14. To actually form the ring electrodes 14, the adhesive-metal mixture is preferably wiped onto special non-stick tape, which is wound around the circumference of the elongated tubular body, or body 12, in the desired locations. The tape is removed after the adhesive has cured, leaving a ring electrode 14 securely bonded to the catheter 10. Naturally, the ring electrodes 14 must be mechanically and electrically connected to wires for conducting a current through the ring electrodes 14.

One wire 16 is connected to each ring electrode 14 and threaded through a separate hole 18 in the side wall 15 of the body 12. It may be very difficult to pass the conductor wires 16 through the length of the body 12 due to the small size of the components. To make this process easier, the catheter body 12 is first soaked in a hydrocarbon solvent, such as xylene, toluene, or freon, which greatly swells the catheter body 12 and the size of the holes 18, allowing the wires 16 to be pulled through the holes 18. The solvent also reduces the friction of the catheter body 12. An advance strand, such as a nylon fish line or prolene suture (size 0) is pulled through the hole, tied to the electrode wires, which are then also pulled through the hole. After the solvent is driven off, the catheter body 12 contracts to its original size, shape, and strength. Since the electrode wires 16 are separately implanted in separate lumens in the side wall 15 of the catheter body 12, it is not necessary to insulate them within the side wall 15 of the catheter body 12 and they are also protected from corrosion that might otherwise be caused by bodily fluids. Alternatively, each wire 16 can be insulated with, for example, PTFE, and threaded through a single lumen in the side wall 15 of the body 12, with just enough insulation stripped from the tip of each wire to make contact with a ring electrode 14.

Referring to FIG. 4, each ring electrode 14 is located over a small hole 20 that penetrates a portion of the side wall 15 of the body 12. The wire 16 is threaded through the hole 18 and is pulled through the entire length of the catheter body 12 until the lead line is free from the body 12. The lead line is then detached from the wire 16, which is pulled back through the catheter body 12 (that is, to the left as shown in FIG. 4) until the end 22 of the wire 16 lies within the hole 20. Then the metallic adhesive mixture referred to above is introduced into the hole 20 prior to formation of the ring electrode 14, thus ensuring a good mechanical and electrical bond between each wire 16 and each ring electrode 14. Other fabrication and manufacturing techniques may also be employed to make the catheter.

Referring to FIGS. 1 and 2, the proximal end of the catheter body 12 includes an electrode casing 24, which is canted to one side relative to the longitudinal axis of the catheter body 12 to protect the wires 16 and keep them physically separate from the injection portal 26, which will be discussed in detail below. Each wire 16 is connected to a terminal 28. The terminals 28 are in turn plugged into the terminal block 21 of a conventional electrical pulse generator 19 manufactured for easing pain through electrical stimulation of internal nerve fibers. Two of the four ring electrodes 14 are used at any one time to form a complete electrical circuit with the pulse generator and the bodily tissues and fluids. Customarily, only two electrodes are used at the same time. The particular electrodes to be used for a given application, the precise voltage level, and the frequency of the pulses are all determined empirically through trial and error for each specific case. Broad ranges of frequencies and, however, are normally effective. The voltage is typically within the range of 0.0–10.5 V and frequencies are typically within the range of 0–120 pulses per second. The wires 16 extend from the bottom portion of the electrode casing 24 by about 5 cm so that they can be conveniently connected to the leads of the pulse generator. Typically, the terminals 28 are roughly cylindrical and are adapted to be plugged directly into the receptor terminals of the pulse generator 19.

The wires 16 are preferably stainless steel and each wire 16 comprises a twisted bundle of about 90 strands of 12 micron wire. The wires 16 may be fixed to the terminals 28 by welding or a specialized soldering technique.

The catheter body 12 further includes an aperture 30 at its distal end for administration of an anesthetic that can be injected through the injection portal 26 at the proximate end of the catheter 10. The lengthwise tubular passage, or lumen 17, conveys the pain-relieving agent from the injection portal 26, to the aperture 30 in the distal end. The presence of an anesthetic or narcotic solution inside the catheter body 12 makes it important that the wires 16 and the ring electrodes 14 not communicate with the interior portion of the catheter body 12 because some such solutions conduct electricity. The injection portal 26 is specifically adapted to receive a conventional syringe tip, or I.V. fitting by frictional engagement to prevent leaking or the introduction of air. To use the catheter 10, it is first inserted into the epidural space of the patient through a larger needle by well known techniques. In use in the temporary implantation embodiment, a dilute solution of a pain-relieving agent, such as an anesthetic or a narcotic, may be continually and gradually fed into the catheter body 12, where it provides steady and continuous pain relief when it enters the body. The pain-relieving agent is mixed with or dissolved in water, which acts as a carrier. The pain-relieving mixture or solution may also include other chemicals, such as salts. The pain-relieving agent used in the catheter 10 and the method for alleviating or relieving pain disclosed herein relies on the use of one or more liquid pain-relieving agents, whether dissolved, diluted, suspended or otherwise mixed with a carrier liquid or not. The injection portal 26 is specifically adapted to engage a threaded syringe fitting, although the injection portal 26 may be adapted to fit any desired means for administering a liquid to a patient.

Referring to FIG. 5, there is shown an alternative embodiment of the catheter 10 that is suitable for permanent implantation in a patient for the duration of his life. The catheter 10, the elongated hollow body 12, the ring electrodes 14, the side wall 15, the wires 16 and their terminals 28, the lumen 17, the apertures or holes 18, the small holes 20, and the ends 22 of the wires 16, the aperture 30 and the possible fabrication techniques of the catheter 10 are the same as described above. The permanently implantable epidural catheter with nerve stimulators 31, or pain relief system 31, however, comprises a complete system for the delivery of electrical stimulation and drugs that is wholly embedded within the patient. The self-contained pain relief system 30 includes the catheter 10, an implantable drug delivery pump 32 and an implantable electrical pulse generator 33. The drug pump 32 is connected to the lumen 17 by a drug administration catheter 34 coupled to the catheter 10 by stainless steel connector tube 36. The drug pump 23 may be a mechanical pump that derives its pumping power from a working fluid contained in a sealed chamber filled with a working fluid that encloses a drug reservoir having an expanding bellows portion. Drugs are injected into the drug reservoir, causing the bellows to expand. The working fluid causes the bellows to compress gradually, squeezing the drug through the lumen 17 and into the patient. Infusion flow rates are commonly set at 1.0–6.0 ml/day, and cannot be adjusted or programmed after implantation. Such a drug pump is currently available from Infusaid Corporation of Norwood, Mass., U.S.A. In the preferred embodiment, the drug pump 32 includes a drug reservoir 38 and a drug injection portal 40 that is a membrane that can be penetrated by a needle to permit subcutaneous replenishment of the drug by injection into the reservoir 38. The preferred drug pump 32 is includes an electrically operated pump powered by a self-contained battery and can be programmed to increase or decrease the drug dosage via an electrical induction programming device that is held close to the patient's skin. A programmable drug pump 32 provides dramatic flexibility in treatment because it allows the use of different drugs and different dosages. Such a preferred pump is currently available from Medtronic, Incorporated of Minneapolis, Minn., U.S.A.

The pain relief system 31 further includes the implantable electrical pulse generator 33, connected to the wires 16 of the catheter 10 by the lead set 40, which includes the connector blocks 44, into which the terminals 28 of the catheter 10 are connected. The pulse generator 33 is preferably a self-contained light-weight unit powered by an internal battery and capable of being programmed electronically by electrical induction through the skin after implantation. All the operating parameters of the pulse generator 33 can be adjusted after implantation if necessary to improve the quality of pain relief. Such a programmable electrical pulse generator is currently available from Medtronic Incorporated of Minneapolis, Minn., U.S.A. In use, the catheter 10 is implanted and then the two ring electrodes that provide the best pain relief are selected as previously described. Those two terminals 28 are then connected to the connector blocks 44. The entire system 31 is then implanted and the opening in the patient is closed. The two terminals 16 that are not connected to the pulse generator can be left loose inside the patient or snipped off. If they are left loose, it is relatively easy to open the patient and connect a different pair of terminals 16 to the patient, if desired.

Alternatively, all four terminals 44 may be connected to a single connector block and the two ring electrodes offering the best pain relief can be selected and programmed for use electronically by electrical induction through the skin. Referring to FIG. 6, an alternative connector block is shown, having a female terminal block 46, which is engaged by a male terminal block 47. A four wire lead set 48 is connected to the pulse generator 33 from the female terminal block 48. The wires 16 from the catheter 10 are connected into receptacles in the male terminal block 47.

Either embodiment of the epidural catheter with nerve stimulators 10 may be employed in a variety of methods for relieving pain. In general, the electrical pulse stimulation available through the ring electrodes 14 may be used in conjunction with either narcotics or anesthetics for the general relief of pain. In the methods of using the catheter 10, electrical stimulation and pain-relieving agents may be used in any order. The treatment modality that works best with each particular patient in a particular phase of treatment for pain from a particular illness can be determined from empirical feedback from the patient.

In particular, the anesthetic or narcotic, or other pain-relieving agent is preferably in the liquid state. In the liquid state, the pain-relieving agent can be administered continuously in diluted form through the injection portal 26 to the aperture 30 in the distal end of the catheter 10 through the lumen 17. Thus, one process for relieving pain using the catheter 10 is the continuous controlled dosage of an anesthetic or narcotic into the epidural space of the patient. Secondly, electrical stimulation of the nerves in the epidural space can be used to relieve pain, particularly in the type C nerve fibers of the spinal nerves by pulsing any two of the four ring electrodes 14. Third, the electrical stimulation by the ring electrodes 14 may be employed simultaneously with the administration of a pain-relieving agent, such as a narcotic or an anesthetic. Fourth, the pain-relieving agent may be administered independently of and without electrical stimulation or prior to electrical stimulation. Fifth, electrical stimulation through the electrodes 14 may be practiced and then halted, thereafter the treatment being made with a narcotic or anesthetic on an episodic or continuous basis.

The effectiveness of either the temporary use or permanent embodiment is enhanced when different treatment modes are employed in different sequences to best treat the patient. The catheter 10 of the pain relief system 31 both provide an effective treatment for certain types of cancer patients whose pain is so profound that only strong narcotics will alleviate it. Unfortunately, however, patients treated with epidural narcotics develop a tolerance for these drugs in which no amount of narcotic administered into the epidural space will effectively control pain, leaving the physician no option for relieving the patient's pain. Using the catheter 10 in either embodiment, the physician can easily stop administering narcotics, and resort to local anesthetic with electrical stimulation until the state of narcotics tolerance disappears. Then narcotic treatment can resume. It is not necessary to make repeated entries into the epidural space to carry out such a regimen.

Similarly, the catheter 10 can be used to help prepare for surgery, as well as for post-surgical pain control. The catheter 10 can be inserted into the epidural space, and then a local anesthetic is injected to establish a painless state for the surgery. Neither narcotics or electrical stimulation can facilitate anesthesia to enable the surgeon to operate on the patient. After the surgery, however, narcotics are delivered through the lumen for post operative pain relief. This avoids the necessity for having to invade the epidural space twice, sparing the patient additional pain and reducing the extent of epidural scarring, which interferes with subsequent efforts to provide pain relief, especially by reducing the effectiveness of electrical stimulation.

In another treatment method using the catheter 10, the patient first receives electrical stimulation, followed by a liquid pain-relieving agent, which is preferably a narcotic. In this method, the patient receives epidural electrical stimulation first because electrical stimulation is superior in its quality of pain control to either narcotics or local anesthetics, which may be added at a later time as an adjunct therapy when electrical stimulation fails to achieve adequate pain control. Such failure may occur either because of electrode migration in the epidural space, or the growth of fibrous tissue covering the electrodes, which increases electrical resistance at the junction between the electrodes and the bodily tissue, preventing sufficient electrical dosages from reaching the nerves. Using the catheter 10 in this method makes it possible to administer either electrical stimulation or liquid pain-relieving agent therapy without having to reintroduce another catheter at a later time, which may be difficult because of the aforementioned scarring in the epidural space.

In short, methods of relieving pain that employ the catheter 10 bring a flexibility in treatment modalities to the patient that has not been present before. Even if or when electrical stimulation is no longer necessary for pain control, or does not adequately control pain, the catheter 10 may remain inside the patient's body and continue to provide a valuable pathway for the administration of other pain-relieving agents. The availability of the catheter 10 for performing this function reduces the trauma to the patient because subsequent provisions for relieving pain do not require further invasion of the patient's body, thereby reducing the risk of infection and the general discomfort to the patient. In addition, placement of the epidural catheter in the epidural space delivers the pain-relieving agent directly to the best possible location for the relief of pain resulting from many types of surgery or illnesses.

It is to be understood that while certain forms of this invention have been illustrated and described, it is not limited thereto, except in so far as such limitations are included in the following claims.

Having thus described the invention, what is claimed as new and desired to be secured by Letters Patent is as follows:

1. A method of pain treatment carried out in the epidural spaces of a patient comprising:

(a) implanting an apparatus for pain relief into a patient, said apparatus comprising three discrete interconnected elements; (i) a catheter implanted in the epidural spaces of said patient, (hi) a battery operated drug pump having a drug reservoir comprising a membrane whereby a liquid pain-relieving agent may be injected through the patient's skin into said reservoir to replenish a supply of a pain-relieving agent in said reservoir, said drug pump further comprising means for delivering said liquid pain-relieving agent to a lumen in said catheter, and (iii) a battery operated electrical pulse generating means operatively connected to a plurality of ring electrodes on said catheter; said catheter comprising means for administering said liquid pain-relieving agent to said patient further comprising an elongated hollow body having a distal end and a proximal end, said lumen therebetween, said body further comprising a first opening at said proximal end and a second opening at said distal end whereby said liquid pain-relieving agent is introduced through said first opening by said delivering means of said drug pump, flows through said lumen and out of said second opening into the patient, at least two ring electrodes spaced downwardly from said distal end on the exterior surface of said lumen and electrically insulated from one another, a separate wire connected to each said ring electrode, each said wire being embedded in the wall of said elongated hollow body from each said electrode to said proximal end of said elongated hollow body and terminating in a separate terminal external to said lumen, and operatively connected to said electrical pulse generating means for administering electrical pulses to said ring electrodes for pain relief in the patient;

(b) pulsing electricity through at least two said ring electrodes of said catheter in a manner consistent with relieving pain;

(c) continually and gradually delivering said liquid pain-relieving agent from said drug pump through said lumen into the epidural spaces of said patient through said drug delivery means of said drug pump;

(d) leaving said catheter in place in the epidural spaces of the patient for an indefinite lengthy period of at least three days, thereby providing steady and continuous pain relief to the patient.

2. A method in accordance with claim 1, wherein said step (c) of delivering said liquid pain-relieving agent comprises delivering an anesthetic.

3. A method in accordance with claim 1, wherein said step (c) of delivering said liquid pain-relieving agent comprises delivering a narcotic.

4. A method in accordance with claim 1, wherein said step (c) of delivering said liquid pain-relieving agent comprises delivering an anesthesia.

5. A method in accordance with claim 1, wherein said step of delivering said pain-relieving agent further comprises the step of replenishing the supply of said liquid pain-relieving agent in said reservoir by injecting said liquid pain-relieving agent into said reservoir through said membrane.

6. A method in accordance with claim 1, wherein step (c) is performed prior to performing step (b).

7. A method in accordance with claim 1, wherein steps (b) and (c) are performed simultaneously.

8. A method in accordance with claim 1, wherein said catheter comprises four said ring electrodes, each of said ring electrodes connected to a separate terminal by a separate wire, and further comprising the steps of selecting two of said ring electrodes for operative connection to said electrical pulse generator that provide the greatest degree of pain relief for the patient.

9. A method in accordance with claim 1, wherein said step of delivering said liquid pain-relieving agent further comprises a step of dripping said liquid pain-relieving agent through said lumen into the epidural spaces of said patient.

10. A method in accordance with claim 1, further comprising the additional step of replenishing said reservoir of said drug pump with a liquid pain-relieving agent different from a liquid pain-relieving agent previously stored in said reservoir.

11. A method in accordance with claim 1 further comprising changing the rate of delivery of said pain-relieving agent from said drug pump to said catheter during a course of treatment in response to patient feedback.

12. A method in accordance with claim 1 further comprising the step of changing the frequency and duration of electrical pulses delivered by said electrical pulse generating means in step b.

13. A method of pain treatment for chronic pain carried out in the epidural spaces of a patient comprising the sequential steps of:

(a) implanting an apparatus for pain relief into said patient, said apparatus comprising three interconnected elements; (i) said catheter implanted in the epidural spaces of a patient, (ii) a battery operated drug pump having a drug reservoir comprising a membrane whereby a liquid pain-relieving agent may be injected through the skin of said patient into said reservoir to replenish a supply of said pain-relieving agent in said reservoir, said drug pump further comprising drug delivery means for delivering said pain-relieving agent to a lumen in said catheter, and (iii) a battery operated electrical pulse generating means operatively connected to a plurality of ring electrodes on said catheter; said catheter comprising means for administering said liquid pain-relieving agent to said patient further comprising an elongated hollow body having a distal end and a proximal end, said lumen therebetween, said body further comprising a first opening at said proximal end and a second opening at said distal end whereby said liquid pain-relieving agent is introduced through said first opening by said drug delivery means of said drug pump, flows through said lumen and out of said second opening into said patient, at least two ring electrodes spaced downwardly from said distal end on an exterior surface of said lumen and electrically insulated from one another, a separate wire connected to each said ring electrode, each said wire being embedded in a side wall of said elongated hollow body from each said electrode to said proximal end of said elongated hollow body and terminating in a separate terminal external to said lumen, and operatively connected to said electrical pulse generating means for administering electrical pulses to said ring electrodes for pain relief in said patient;

(b) continually and gradually delivering a narcotic through said lumen into said epidural spaces of said patient through a delivery means connected to said proximal end of said lumen until toxic doses of said narcotic no longer controls pain effectively and a state of tolerance develops in said patient;

(c) terminating delivery of said narcotic through said lumen when said state of tolerance has developed;

(d) continually and gradually administering a local anesthetic through said lumen into said epidural spaces of said patient through said drug delivery means connected to said proximal end of said lumen until said tolerance for said narcotic disappears;

(e) pulsing electricity through at least two said terminals in a manner consistent with relieving pain simultaneously with step (d), until said tolerance of said narcotic disappears; and (f) resuming delivery of said narcotic, terminating said step of pulsing of electricity through said electrodes, and terminating said step of administering a local anesthetic; thereby providing steady and continuous pain relief to said patient.

14. A process in accordance with claim 13, wherein said local anesthetic administered in step (d) is a non-narcotic anesthetic.

15. A method in accordance with claim 13, wherein said step of delivering said pain-relieving agent further comprises the step of replenishing said supply of said liquid pain-relieving agent in said reservoir by injecting said pain-relieving agent into said reservoir through said skin of said patient and through said membrane.

16. A method in accordance with claim 13, wherein said catheter comprises four said ring electrodes, each of said ring electrodes connected to a separate terminal by a separate wire, and further comprising the steps of selecting two of said ring electrodes for operative connection to said electrical pulse generator that provide the greatest degree of pain relief for said patient.

17. A method in accordance with claim 13 further comprising the additional step of replenishing said reservoir of said drug pump with a liquid pain-relieving agent different from said liquid pain-relieving agent previously stored in said reservoir.

18. A method in accordance with claim 13 further comprising changing the rate of delivery of said pain-relieving agent from said drug pump to said catheter during a course of treatment in response to patient feedback.

19. A method in accordance with claim 13 further comprising the step of changing the frequency and duration of electrical pulses delivered by said electrical pulse generating means in step b.

* * * * *